United States Patent [19]

Roberts

[11] Patent Number: 5,023,107
[45] Date of Patent: Jun. 11, 1991

[54] HARD TISSUE SURFACE TREATMENT

[75] Inventor: Thomas A. Roberts, Cheshire, United Kingdom

[73] Assignee: Imperial Chemical Industries PLC, London, England

[21] Appl. No.: 346,806

[22] Filed: May 3, 1989

[30] Foreign Application Priority Data

May 3, 1988 [GB] United Kingdom ............... 8810412

[51] Int. Cl.$^5$ .............................................. A61C 13/23
[52] U.S. Cl. ..................................... 427/2; 433/228.1; 523/116; 564/235; 564/236; 564/238; 564/291
[58] Field of Search ...................... 427/2; 433/228.1; 523/116; 528/422; 564/235, 236, 238, 291

[56] References Cited

U.S. PATENT DOCUMENTS

| | | | |
|---|---|---|---|
| 4,053,636 | 10/1977 | Eustis, III et al. | 564/235 |
| 4,067,962 | 1/1978 | Juneja | 564/235 |
| 4,198,392 | 4/1980 | Juneja | 564/235 |
| 4,567,174 | 1/1986 | Edwards et al. | 564/235 |

FOREIGN PATENT DOCUMENTS

| | | | |
|---|---|---|---|
| 7606824 | 12/1976 | Netherlands | 564/235 |
| 702268 | 1/1954 | United Kingdom | |
| 705838 | 3/1954 | United Kingdom | |
| 1095902 | 12/1967 | United Kingdom | |
| 1369942 | 10/1974 | United Kingdom | 564/235 |
| 8000057 | 1/1980 | World Int. Prop. O. | |

OTHER PUBLICATIONS

J. Dent. Res., 61(12), 1416–1422, (1982), Powis et al.
Scand. J. Dent. Res., 87(4), 309–317, (1979), Eriksen et al.

*Primary Examiner*—Norman Morgenstern
*Assistant Examiner*—Terry J. Owens
*Attorney, Agent, or Firm*—Cushman, Darby & Cushman

[57] ABSTRACT

A method of improving the adhesion of an adhesive to the surface of hard tissue. Before the adhesive is applied, the hard tissue surface is primed with a polybiguanide or an addition salt thereof, or is pretreated with an aqueous solution of a magnesium salt and then primed with a primer selected from a long chain alkyl quaternary ammonium salt, a bisbiguanide, an acid addition salt of a bisbiguanide, a polybiguanide, and an acid addition salt of polybiguanide.

9 Claims, No Drawings

HARD TISSUE SURFACE TREATMENT

This invention relates to the treatment of the surface of hard tissue such as dentin.

The use of adhesives that bond to hard tissues such as for example dentin have become of increasing interest in the dental area. In some instances these are associated with the use of acid etchants such as for example phosphoric acid but this is generally not desirable in such a sensitive environment. The American Dental Association recommends against the use of such phosphoric acid pretreatment.

Adhesive compositions and in particular polymerizable adhesive compositions may be used as liners to which restorative dental filling compositions may be applied and as primers onto which may be applied dental adhesives for mounting for example orthodontic brackets or crowns.

Amalgam and restorative dental filling compositions do not adhere well to tooth surface. In filling a dental cavity, the problem of poor adhesion can be ameliorated by preparing undercut cavities so as improve mechanical retention of the filling. In the case of enamel surfaces, mechanical keying can be improved on a smaller scale by etching the surface with phosphoric acid. However a truly adhesive system would enable the dentist to improve operative procedures. The use of phosphoric acid could be greatly reduced or even eliminated in some instances; restorative procedures involving removal of dentin could be carried out with a much reduced level of removal of vital tissue; marginal leakage might be reduced.

It has to be borne in mind that an adhesive system is associated with bone and teeth which are real materials, that is, it is associated with living, dynamic tissue, and as such any adhesive is likely to be the result of a compromise between competing influences. For example, to adhere to the surface of a tooth requires hydrophilic groups but their presence increases the probability that the adhesive will be hydrolytically unstable. Nevertheless a number of adhesives are available to the practitioner and almost all are based on organic phosphate esters. It is highly desirable therefore that the active adhesive component have a low concentration in the adhesive composition and hence that component needs to have high adhesive properties. The composition should have low viscosity so that it readily flows over the surface to be bonded. European patent specification 0 074 708 discusses a considerable number of patent specifications in which various ethylenically unsaturated phosphorus esters are described as adhesives. In that specification particular phosphate esters based on a long chain alkyl ester of acrylic and methacrylic acids are claimed and said to have improved adhesive properties in dental applications. That specification states that 2-methacryloyloxyethyl dihydrogen phosphate is a comparatively poor adhesive component and causes blistering in a paint film. European patent application 0 115 948 describes the use of organic pyrophosphate esters as polymerizable adhesive components. European patent applications 0 058 483 and 0 132 318 describe the use of halophosphorus acid esters as polymerizable monomers in a dental adhesive; these esters contain at least one ethylenically unsaturated functional group and a chlorine or bromine atom attached directly to the phosphorus atom.

U.S. Pat. No. 4,044,044 described the use of phosphate esters of hydroxy acrylates as components in anaerobic adhesive compositions. Those compositions are said to remain in a liquid state as long as they remain in contact with air whilst they are said to cure rapidly by polymerization under the exclusion of air. Those adhesive compositions are useful as loosening-prevention materials particularly at high pressure.

The adhesive properties associated with polymerizable esters of phosphorus acid are dependant upon the level of impurity in the particular ester. If a dihydrogen phosphate ester is substantially free of phosphoric acid, the monohydrogen ester and the fully esterified ester, then the resultant adhesive composition is surprisingly effective as an adhesive in aqueous environment. Particularly suitable adhesive compositions which are curable rapidly in the presence of air are single-component, visible light-curable liquid adhesive compositions which comprise:

(a) 2 to 20 parts by weight of at least one substantially pure phosphate ester having the formula $CH_2=C(R^1).CO.O.R^2.OP(O)(OH)^2$ in which $R^1$ is a hydrogen atom or a methyl group, and $R^2$ is $-CH_2-CH_2-$, $CH_2-CH(CH_3)-$ or $-CH(CH_3)-CH_2-$, and (b) 98 to 80 parts by weight of at least one ethylenically unsaturated monomer copolymerizable with the phosphate ester, and an effective amount of visible light activated catalyst, as described in our copending UK patent application 8725324, the disclosure of which is disclosed herein by way of reference.

It has now been found that if the surface of the hard tissue is contacted with a selected primer before being coated with an adhesive then the adhesive strength of the cured adhesive to the hard tissue is surprisingly increased. The use of a primer may also reduce any deterioration in adhesive strength found on using an adhesive which had been stored for a prolonged period.

The primer is preferably a long chain alkyl quaternary ammonium salt, bisbiguanide, most preferably a polybiguanide.

Suitable bisbiguanides include compounds having the formula:

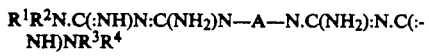

$$R^1R^2N.C(:NH)N:C(NH_2)N-A-N.C(NH_2):N.C(:NH)NR^3R^4 \qquad I$$

wherein either:

(i) $R^1$ and $R^3$, which may be the same or different, are each a phenyl radical which is substituted by alkyl, alkoxy, nitro or halogen, $R^2$ and $R^4$ are both hydrogen, and A is a 3-9C polymethylene diradical, wherein the polymethylene chain may be interrupted by oxygen atoms and/or by aromatic nuclei; or (ii) the bivalent bridge A is:
(a) alkylene of from 2 to 12 carbon atoms having the valence bonds attached to different carbon atoms,
(b) $-(CH_2)_m-X-(CH_2)_n-$ wherein m and n each represent an integer from 2 to 6 and X is O or S,

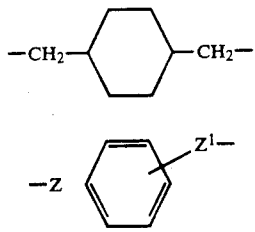
(c)

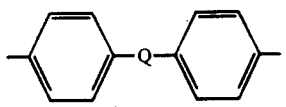
(d)

wherein Z and Z¹ are each alkylene of from 1 to 3 carbon atoms,

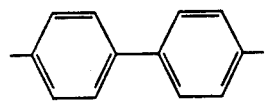

wherein Q is —O—, —S—, —SO— or —SO$_2$—,

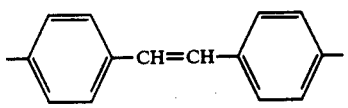
(f)

or

R¹ and R³ are each:
(a) alkyl of from 6 to 16 carbon atoms, or
(b) alkyl-Y-alkylene, wherein Y is O or S and the alkyl and alkylene radicals together contain 3 to 15 carbon atoms;
and R² and R⁴ are each hydrogen or 1-6C alkyl; or and acid addition salt thereof.

Bisbiguanide compounds of the formula I wherein the substituents have the values given in (i) are fully described in United Kingdom Patent Number 705,838, and those wherein the substituents have the values given in (ii) are fully described in United Kingdom Patent Number 1,095,902, and all the said compounds of the formula I are described as bactericides or plant fungicides.

Preferred bisbiguanide compounds of the formula I for use in the above method are chlorhexidine (I, R¹=R³=p-chlorophenyl, R²=R⁴=hydrogen, A=—(CH$_2$)$_6$—) and the compound I, (R¹=R³=2-ethyl-hexyl, R²=R⁴=hydrogen, A=—(CH$_2$)$_6$—) or an acid-addition salt thereof, especially the dihydrochlorides, diacetates and digluconates.

Preferred bisbiguanide compounds of the formula I for use in this aspect of the invention are those wherein X and Y are each —(CH$_2$)$_2$— to —(CH$_2$)$_{12}$—, and preferably each is —(CH$_2$)$_6$—, and which have a number average molecular weight of about 500 to 20,000 and the salts thereof, especially the dihydrochloride, diacetate and digluconate.

Suitable polymeric biguanides include biguanide compounds which in the form of free base have a linear polymer form in which the recurring unit is represented by the formula:

$$-X.NH.C(:NH)NH.C(:NH)N-H.Y.NH.C(:NH)NH.C(:NH)NH-$$ II wherein X and Y stand for bridging groups in which together the total number of carbon atoms directly interposed between the adjacent nitrogen atoms is greater than 9 and less than 17, or an acid-addition salt thereof.

The said bridging groups may consist of poly-methylene chains, which optionally may be interrupted, as by oxygen or sulphur atoms, and also they may incorporate cyclic nuclei which themselves may be saturated or unsaturated. The number of carbon atoms directly interposed between the nitrogen atoms when the groups X and/or Y incorporate a cyclic group or groups includes those in that segment of the cyclic group or groups which is the shortest.

The biguanides of the formula II are fully described in United Kingdom Patent Number 702,268, and are stated to possess good antibacterial activity.

A preferred polymeric biguanide for use in the process of the invention is that wherein X is —(CH$_2$)$_2$— to —(CH$_2$)$_{12}$—, preferably —(CH$_2$)$_6$—, Y is —(CH$_2$)$_2$— to —(CH$_2$)$_{12}$—, preferably —(CH$_2$)$_6$), and which has a number average molecular weight of about 500 to 20,000, and especially preferred is a mixture of polymeric biguanides of the formula:

$$[-(CH_2)_6-NH.C(:NH).NH.C(:NH)NH-]_n$$ III wherein n varies from about 5 to 10, and having a number average molecular weight of about 1000 to 2200, in the form of their salts with hydrochloric acid.

The long chain alkyl quaternary ammonium salt preferably has the formula (R⁵)$_4$NZ wherein one of the radicals R⁵ is an alkyl group containing 10 to 20 carbon atoms (and including a mixture thereof which averages to 10 to 20 carbon atoms), the other three radicals R⁵ which may be the same or different are alkyl or alkaryl groups containing 1 to 4, preferably 1, alkyl carbon atoms and Z is a halide, preferably chloride or bromide.

The primer has concentration of 0.01% to 5%, preferably 0.05 to 2%, by weight (in 100 cm³ of solution). The solvent is preferably water but may include any clinically acceptable co-solvent. Typical co-solvents are alcohols containing 1 to 4 carbon atoms and mixtures thereof including industrial methylated spirit.

The primer may be applied to the hard tissue by any convenient means. It may be applied for example by immersing, brushing, rinsing, spraying, swabbing. If the hard tissue is in the mouth, a convenient application method is by the use of a mouthwash.

After the primer has been applied to the surface on the hard tissue, the surface is preferably dried, conveniently by the use of compressed gas, e.g., air. The adhesive is then applied to the so-treated surface and cured in the conventional way.

In a preferred embodiment the hard tissue surface may be pretreated with an aqueous solution of a magnesium salt, such as for example a halide, preferably chloride, sulphate followed by drying of the so-pretreated surface. By aqueous is meant a solvent which is essentially water but may contain other clinically acceptable solvents.

Hence a preferred sequence of steps is as follows:
Drill out cavity
Pretreatment with a magnesium salt solution
Dry Apply primer
Dry
Apply adhesive
Cure
Apply composite
Cure Preferred adhesives are unsaturated esters of phosphoric acid, such as for example those hereinbefore described. It is preferable that adhesive compositions are cured by irradiation by visible light and hence such compositions should contain the appropriate catalyst system.

In a preferred adhesive composition the phosphorus ester component is preferably 2-methacryloyloxy-propyldihydrogen phosphate. This may be prepared by for example reacting hydroxy alkylacrylate (or methacrylate) with at least an equimolar amount of phosphorus oxychloride in the presence of a tertiary amine, followed by hydrolysis of any remaining chlorine-phosphorus bonds. The dihydrogen phosphorus ester is then purified by a series of wash and extraction stages so that the ester is substantially pure, i.e., free of other esters of phosphorus acid so that such impurity level is less than 5% by weight, preferably less than 2% by weight. The adhesive compositions of the present invention preferably contain at least one ethylenically unsaturated monomer compolymerizable with the phosphate ester. The viscosity characteristics of the adhesive composition such as viscosity itself and flow and wetting properties are largely determined by those of the monomer. A wide range of monomer(s) is suitable for use in adhesive compositions. The most frequently used monomers include those of the (meth)acrylate, vinyl urethane and styrene types and vinyl acetate. However other monomers such as (meth)acrylamides, vinyl ethers, fumarates, maleates, vinyl ketones, vinyl nitriles, vinyl pyridines and vinyl naphthalenes may also be used either alone or in combination provided that the viscosity of the composition is appropriate. The concentration of phosphate ester in the adhesive composition is preferably 5% by weight or more, and preferably no greater than 15% by weight. Vinyl esters suitable include, for example, vinyl acetate and esters of acrylic acid having the structure $CH_2=CH-COOR^6$, where $R^6$ is an alkyl, aryl, alkaryl, aralkyl or cycloalkyl group. For example, $R^6$ may be an alkyl group having from 1 to 20, and preferably 1 to 10 carbon atoms. Particular vinyl esters which may be mentioned include, for example, methyl acrylate, ethyl acrylate, n- and isopropyl-acrylates, and n-, iso- and tertiary butyl acrylates. Other suitable vinyl esters include, for example, esters of the formula:

$$CH_2=C(R^7)COOR^6$$

where $R^7$ is methyl. In the ester of formula:

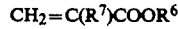
$$CH_2=C(R^7)COOR^6$$

$R^6$ and $R^7$ may be the same or different.

Particular vinyl esters which may be mentioned include, for example methacrylate, ethyl methacrylate, n- and isopropyl-methacrylate, and n-, iso- and tertiary butyl methacrylate vinyl, esters such as n-hexyl, cyclohexyl and tetrahydrofurfuryl acrylates methacrylates. The monomers should have low toxicity. Suitable aromatic vinyl compounds of the styrene type include, for example, styrene and derivatives thereof, e.g. α-alkyl derivatives of styrene, e.g. α-methyl styrene, and vinyl toluene.

Suitable vinyl nitriles include, for example, acrylonitrile and derivatives thereof, e.g. methacrylonitrile.

Other suitable ethylenically unsaturated monomers include vinyl pyrrolidone, and hydroxyalkyl acrylates and methacrylates, e.g. hydroxyethyl acrylate, hydroxypropylacrylate, hydroxyethylmethacrylate and hydroxypropyl-methacrylate.

Polyfunctional monomers are also suitable as polymerization materials, that is, monomers containing two or more vinyl groups. Suitable monomers include, for example, glycol dimethacrylate, diallyl phthalate, and triallyl cyanurate.

The ethylenically unsaturated material may include at least one ethylenically unsaturated polymer, suitably in combination with at least one ethylenically unsaturated monomer.

The adhesive composition is preferably free from volatile solvent. However if a solvent is included, then the following polymerizable material may also be present provided that the viscosity of the composition is appropriate and most preferably less than 25 centipoise at 25° C.

Such polymerizable materials are preferably liquid ethylenically unsaturated material such as vinyl urethane for example those described in British patent specifications 1352063, 1465097, 1498421 and German Offenlegungsschrift 2419887 or the reaction product of a diol such as glycol but particularly a bisphenol with a gylcidyl alkacrylate such as those described for example in U.S. Pat. No. 3066112 and 4131729 (the disclosure in these specifications are incorporated herein by way of reference).

A preferred reaction product of a glycidyl alkacrylate and a diol has the formula:

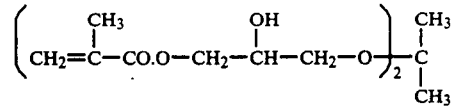

Preferred vinyl urethanes described in the aforesaid British patent specifications and German Offenlegungsschrift are the reaction product of a urethane prepolymer and an ester of acrylic or methacrylic acid with a hydroxy alkanol of at least 2 carbon atoms, the urethane prepolymer being the reaction product of a diisocyanate of the structure $OCN-R^8-NCO$ and a diol of the structure $HO-R^9-OH$ wherein $R^8$ is a divalent hydrocarbyl group and $R^9$ is the residue of a condensate of an alkylene oxide with an organic compound containing two phenolic or alcoholic groups.

Other suitable vinyl urethanes include those made by the reaction of alkyl and aryl, preferably alkyl, diisocyanates with hydroxy alkyl acrylates and alkacrylates such as those described in British patent specifications 1401805, 1428672 and 1430303 (the disclosures of which are included herein by way of reference).

The adhesive compositions are preferably cured by irradiating the composition with visible radiation, preferably that having a wavelength in the range 400 mμ to 500 mμ. In order that curing of the compositions may be achieved in that range the compositions contain a catalyst which is activated by visible light. Such a catalyst preferably contains at least one ketone selected from fluorenone and diketone and at least one organic peroxide.

Ketones suitable for use in the composition of the present invention also show some photosensitive catalytic action on their own without the presence of organic peroxide. Such activity of the ketone is enhanced by the addition of a reducing agent as described in the German Offenlegungsschrift 2251048. Accordingly the present ketones are selected from fluorenone and α-diketones and their derivatives which in admixture with a similar amount of organic amine which is capable of reducing that ketone when the latter is in an excited state, but in the absence of organic peroxide, catalyse cure of an ethylenically unsaturated material. Evidence of cure may be absence of organic peroxide, catalyse cure of an ethylenically unsaturated material. Evidence of cure may be conveniently detected by examining the change in viscosity of a mixture of the ethylenically unsaturated material containing the ketone and organic amine each at 1% by weight based on ethylenically unsaturated material using an oscillating rheometer, samples thickness 2 mm., whilst the mixture is being irradiated with light having wavelength in the range 400 to 500 mμ. Such an examination may be carried out using the method described British Standard 5199: 1975, paragraph 6.4 provided that provision is made to allow visible light to be directed onto the mixture. Preferably the ketone has a cure time of less than 15 minutes at a radiation level of 1000 w/m² as measured at 470 mμ, bandwidth ±8 mμ, for example using a Macam Radiometer (Macam Photometrics Ltd., Edinburgh, Scotland).

Diketones have the formula:

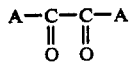

in which the groups A, which may be the same or different, are hydrocarbyl or substituted hydrocarbyl groups and in which the groups A may be further linked together by a divalent link or by a divalent hydrocarbyl or substituted hydrocarbyl group or in which the groups A together may form a fused aromatic ring system. Preferably the groups A are the same.

The groups A may be aliphatic or aromatic. Within the scope of the term aliphatic are included cycloaliphatic groups and aliphatic groups which carry aromatic substituents, that is, aralkyl groups. Similarly within the scope of the term aromatic group are included groups which carry alkyl substituents, that is, alkaryl groups. Within the term aromatic groups are included heterocyclic groups.

The aromatic group may be a benzenoid aromatic group, e.g. the phenyl group, or it may be a non-benzenoid cyclic group which is recognized in the art as possessing the characteristics of a benzenoid aromatic group.

The groups A, especially when aromatic may carry substituent groups other than hydrocarbyl, e.g. halogen or alkoxy. Substituents other than hydrocarbyl may result in inhibition of polymerization of ethylenically unsaturated materials, and if the α-diketone contains such substituents it preferably is not present in the photopolymerizable composition in such a concentration as to result in substantial inhibition of polymerization of the ethylenically unsaturated material in the composition.

The groups A may be further linked together by a direct link, or by a divalent group, e.g. a divalent hydrocarbyl group, that is, in addition to the link through the group.

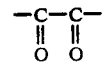

the groups A may be further linked so as to form a cyclic ring system. For example, where the groups A are aromatic the α-diketone may have the structure

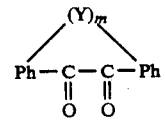

in which Ph is a phenylene group, Y is >CH₂, or a derivative thereof wherein one or both of the hydrogen atoms are replaced by a hydrocarbyl group, and m is 0, 1, or 2. Preferably the group Y is linked to the aromatic groups in positions ortho to the group.

The groups A together may form a fused aromatic ring system.

In general, α-diketones are capable of being excited by radiation in the visible region of the spectrum, that is, by light having a wavelength greater than 400 mμ, e.g. in the wavelength range 400 mμ to 500 mμ. For the present invention, α-diketone should have low volatility so as to minimize odor and concentration variation. Suitable α-diketones include benzil in which both the groups A are phenyl, α-diketones in which both of the groups A are fused aromatic, e.g. α-naphthil and β-naphthil, and α-diketones in which the groups A are alkaryl groups, e.g. p-tolil. As an example of a suitable α-diketone in which the groups A are non-benzenoid aromatic there may be mentioned furil, e.g. 2:2'-furil. Derivatives of the α-diketone in which the groups A carry non-hydrocarbyl groups as for example p,p'-dialkoxy benzil, e.g. p,p'-dimethoxy benzil or p,p'-dihalobenzil, e.g. p,p'-dichlorobenzil, or p-nitrobenzil may be incorporated.

The groups A may be linked together by a direct link or by a divalent hydrocarbyl group to form a cyclic ring system. For example, where the groups A are aliphatic the α-diketone may be camphorquinone.

An example of an α-diketone having the structure I is phenanthraquinone in which the aromatic groups A being linked by a direct link ortho to the group

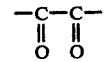

Suitable derivatives include 2-bromo-, 2-nitro, 4-nitro, 3-chloro-, 2,7-dinitro-, 1-methyl-7-isopropyl phenanthraquinone.

The α-diketone may be acenaphthene quinone in which the groups A together form a fused aromatic ring system.

The ketone may also be fluorenone and its derivatives such as for example lower alkyl (Cl-6), halo, nitro, carboxylic acid and esters thereof, particularly in the 2- and 4- positions.

The ketone may, for example, be present in the composition in a concentration in the range 0.01% to 2% by weight of the polymerizable material in the adhesive composition although concentrations outside this range may be used if desired. Suitably the ketone is present in a concentration of 0.1% to 1% and more preferably 0.5% to 1% by weight of the ethylenically unsaturated material in composition. The ketone should be soluble in the polymerizable material and the above concentrations refer to solution concentration.

The organic peroxides suitable for use in the present composition include those having the formula $$R^{10}-O-O-R^{10}$$

in which the groups $R^{10}$ which may be the same or different, are hydrogen, alkyl, aryl, or acyl groups, no more than one of the groups R being hydrogen. The term acyl means having the formula $$R^{11}-CO-$$

in which $R^{11}$ is an alkyl, aryl, alkloxy or aryloxy group. The term alkyl and aryl have the definitions given hereinbefore for the groups A and include substituted alkyl and aryl.

Examples of organic peroxide suitable for use in the composition of the present invention include diacetyl peroxide, dibenzoyl peroxide, di-tertiary butyl peroxide, dilauroyl peroxide, tertiary butyl perbenzoate, ditertiary butyl cyclohexyl perdicarbonate.

The organic peroxide may be, for example, present in the composition in the range 0.1% to 10% by weight of the polymerizable material in the composition although concentration outside this range may be used if desired.

The reactivity of a peroxide is often measured in terms of a ten hour half like temperature, i.e. within ten hours at that temperature half of the oxygen has been made available. The peroxides in the adhesive compositions preferably have ten hour half life temperatures of less than 150° C., more preferably less than 100° C.

The rate at which the adhesive composition cures under the influence of visible light can be increased by incorporation into the composition of reducing agent, in concentration 0.1% to 10% by weight of the ethylenically unsaturated monomer, which is capable of reducing the ketone when the latter is in an excited state. Suitable reducing agents are described, for example, in German Offenlegungsschrift 2251048 and include organic amines, phosphites, sulphinic acids.

In general non-basic reducing agents are preferred because they are less likely to react with the phosphate ester.

Suitable non-basic reducing agents include aldehydes and organotin compounds having the formula:

$$(R^{12})_nSn(OR^{13})_m$$

in which n and m are integers having the value 1, 2 or 3 and $n+m=4$, $R^{12}$ is an alkyl or alkenyl group containing 1 to 18 carbon atoms and $R^{13}$ is $R^{12}$ or $R^{12}.CO-$ or having the formula $$([R^{12}]_3Sn)_2O$$

Mixing of the components may be effected by stirring together the polymerizable material together with any filler. It may be useful to dissolve the catalyst components first in the polymerizable material; the polymerizable material may conveniently but less preferably be diluted with a suitable diluent so as to improve solution of the catalyst components. When mixing has been effected the diluent may be removed if desired, e.g. by evaporation. Desirably the present composition is substantially free of solvent because its presence may interfere with adhesion and may give rise to toxicity problems.

Because the photosensitive catalyst renders the polymerizable material and monomer sensitive to light in the 400 mµ to 500 µm visible range, that part of the preparation of the present composition in which photosensitive catalyst is added and subsequent manipulation, e.g. filling of containers should be carried out in the substantial absence of light in that range. Most conveniently, the preparation can be carried out using light outside that range for example under that emitted by sodium vapor electric discharge lamps. It is envisaged that the primer composition for treating the surface of the hard tissue will be packed in small containers (capacity 0.5 to 25 preferably 1 to 10 cm$^3$) which are easy to use in the operating theatre or dental surgery. The container may incorporate a brush, spray or dropper for applying the primer; the container may also include one or a plurality of swabs impregnated with primer. The primer may be co-packed with an adhesive composition which is also preferably packed in single small containers (e.g. 10 g capacity) so as to facilitate handling in the surgery and reduce the risk of inadvertent curing by for example stray light.

The invention is illustrated with reference to the following Examples:

EXAMPLE 1

(a) Preparation of phosphate ester

Phosphorus oxychloride (127.9 g; 0.83 moles) was mixed with methylene chloride (600 cm$^3$). The mixture was stirred and cooled to 0° C. A mixture of hydroxypropyl methacrylate (120 g; 0.83 moles), pyridine (65.8 g; 0.83 moles) and methylene chloride (400 cm$^3$) was added dropwise to the phosphorus oxychloride mixture over a period of 45 minutes whilst keeping the reaction temperature in the range 0° to 3° C. The mixture was stirred for a further 2 hours within that temperature range. The reaction mixture was then poured into 1 liter cold water and the methylene chloride layer was separated, washed twice with water. The methylene chloride solution was then mixed with water and the methylene chloride removed using a rotary evaporator to leave an aqueous phase and some water insoluble inorganic material. The aqueous layer was washed twice with methylene chloride, and then carefully acidified (hydrochloric acid 208 cm$^3$) with stirring the aqueous phase was then extracted using ethyl acetate (1 liter) and the aqueous phase was rejected. The concentration of phosphate ester was then estimated and analyzed by acid base titration methods and found to contain ester impurity less than 2% weight of 2- methacryloyloxypropyl dihydrogen phosphate. Other ethylenically unsaturated monomer (comonomer) was then added as desired according to the relative concentrations required in the final composition. Ethyl acetate was then removed using a rotary evaporator at 65° C. and under a vacuum of 50 mmHg.

(b) An adhesive formulation was prepared having the following composition:

|  | % w/w |
|---|---|
| Phosphate ester | 9.88 |

-continued

| | % w/w |
|---|---|
| Triethylene glycol dimethacrylate | 88.89 |
| Camphorquinone | 0.74 |
| Dibutyltindilaurate | 0.49 |
| 'Topanol' O | to 200 ppm on final composition. |

The preparation of the composition was carried out under sodium vapor discharge light.

Evaluation of adhesive strength on samples having the above formulations were carried out using the procedure described in British Dental Journal 1984, pages 93 to 95, except that the composite restorative material used in conjunction with the adhesive composition was 'Occlusin' (trade mark, Imperial Chemical Industries PLC). The samples were cured by radiation from a tungsten halogen lamp having a tuned reflector and a dichroic filter which eliminates ultra-violet radiation; the intensity was 1000 $Wm^{-2}$ and cure time was 30 seconds.

'Topanol' is a trade mark of Imperial Chemical Industries PLC and 'Topanol' O is 2,6-ditertiarybutyl-4-methylphenol.

The bond strength to inner dentin tested immediately after preparation of the adhesive was 3.6 MPa; however after the adhesive had been stored for 3 months at room temperature and re-evaluated, the bond strength was found to be 1.8 MPa.

EXAMPLE 2

An adhesive formulation was prepared as described in Example 1, and stored for 7 months at room temperature. Adhesion was evaluated as described in Example 1 but the surface of the dentin was painted with an primer solution, followed by drying using an air blast, before the adhesive formulation was applied.

| Primer | Mean Bond Strength (MPa) |
|---|---|
| 'Corsodyl' | 4.4 |
| Chlorhexidine digluconate (0.2% w/v in 1:1 water/isopropanol) | 3.6 |
| 'Vantocil' (0.1% in water) | 7.4 |
| 'Vantocil' (0.1% in industrial methylated spirit) | 6.5 |
| Cetrimide (1% in water) | 4.4 |

'Corsodyl' and 'Vantocil' are trade marks of Imperial Chemical Industries PLC.
'Corsodyl' comprises 0.2% w/v chlorhexidine digluconate in water.
The 'Vantocil' used in Examples 2 and 3 had the formula III above in which n was 4 to 7.
Cetrimide is cetyltrimethylammonium bromide.

EXAMPLE 3

Some of the treatments described in Example 2 were repeated, but the surface of the dentin was pretreated with magnesium chloride solution (10% w/v in water). The magnesium chloride solution was painted onto the surface of the dentin which was then dried using an air blast. The bond strengths of the adhesive measured using the method described in Example 1 are given in the table below.

| Primer | Mean Bond Strength (MPa) |
|---|---|
| 'Corsodyl' | 7.2 |
| 'Vantocil' (0.1% in water) | 7.6 |

I claim:

1. A method of improving adhesion of an adhesive to the surface of a hard tissue, comprising: priming the surface of the hard tissue with a primer comprising polybiguanide, or an acid-addition salt thereof, before applying the adhesive.

2. A method as claimed in claim 1 in which the primer is applied as a solution of the primer in a clinically acceptable solvent.

3. A method as claimed in claim 2 in which the primer is present in concentration 0.01 to 5% by weight in the solvent.

4. A method as claimed in claim 2 which further comprises a drying stage after applying the primer.

5. A method as claimed in claim 1 which comprises applying the primer to the surface of the hard tissue by immersing, brushing, rinsing, spraying or swabbing the surface with the primer.

6. A method as claimed in claim 1 further comprising pre-treating the surface of the hard tissue with an aqueous solution of a magnesium salt prior to priming the surface.

7. A method as claimed in claim 6 which includes drying the surface of the hard tissue after pre-treating with an aqueous solution of a magnesium salt.

8. A method as claimed in claim 1 in which the hard tissue is dentin.

9. A method of improving adhesion of an adhesive to the surface of a hard tissue which comprises:
 (i) pre-treating the surface of the hard tissue with an aqueous solution of a magnesium salt; and
 (ii) priming the surface of the hard tissue with a primer selected from a long chain alkyl quaternary ammonium salt, bisbiguanide, and an acid addition salt of polybiguanide, before applying the adhesive.

* * * * *